United States Patent [19]

Hueck

[11] Patent Number: 5,038,619
[45] Date of Patent: Aug. 13, 1991

[54] PROCESS AND AN APPARATUS FOR TESTING VEHICLE STABILIZERS

[75] Inventor: Manfred Hueck, Vaterstetten, Fed. Rep. of Germany

[73] Assignee: Industrieanlagen-Betriebsgesellschaft mbH, Ottobrunn, Fed. Rep. of Germany

[21] Appl. No.: 423,396

[22] PCT Filed: Feb. 15, 1988

[86] PCT No.: PCT/EP88/00110
§ 371 Date: Aug. 18, 1989
§ 102(e) Date: Aug. 18, 1989

[87] PCT Pub. No.: WO88/06283
PCT Pub. Date: Aug. 25, 1988

[30] Foreign Application Priority Data

Feb. 19, 1987 [DE] Fed. Rep. of Germany ....... 3705268

[51] Int. Cl.⁵ .............................................. G01N 3/32
[52] U.S. Cl. ........................................ 73/810; 73/808; 73/814; 73/856
[58] Field of Search ................. 73/808, 810, 814, 856, 73/118.1

[56] References Cited

U.S. PATENT DOCUMENTS

| 2,157,903 | 5/1939 | Lapsley | 73/814 |
| 3,664,179 | 5/1972 | Danko et al. | 73/808 |
| 4,283,957 | 8/1981 | Zobrist et al. | 73/814 |

FOREIGN PATENT DOCUMENTS

| 1252700 | 8/1986 | U.S.S.R. | 73/808 |
| 1328736 | 8/1987 | U.S.S.R. | 73/808 |

Primary Examiner—Hezron E. Williams
Assistant Examiner—Rose M. Finley
Attorney, Agent, or Firm—Burgess, Ryan & Wayne

[57] ABSTRACT

A process and an apparatus for testing stabilizers (10) which are supported on stationary bearings (16, 17) upon a bench (32) and which are strained via a drive assembly by movement of one stabilizer leg (12) against the other stabilizer leg (13) includes mass elements (18, 19) attached to stabilizer legs (12, 13), the mass elements (18, 19) being movable via the oscillator exciter (27) attached to one side of the mass element (18) in a manner such that the mass-spring system formed by the stabilizer (10) and mass elements (18, 19) oscillates at its resonant frequency.

11 Claims, 5 Drawing Sheets

PROCESS AND AN APPARATUS FOR TESTING VEHICLE STABILIZERS

BACKGROUND OF THE INVENTION

1. Field of the Invention

The invention is a process and an apparatus for testing stabilizers.

For developing vehicle stabilizers and also for the final inspection of standard parts in the manufacture or inspection departments, vehicle stabilizers must be dynamically tested under stress conditions approximate to those in use. This means, in particular, that the stabilizers are exposed to an endurance test for as many as 1,000,000 stress cycles.

2. Related Art

The known testing stands for stabilizers comprise eccentric drives to introduce the test stress either in opposite directions to both legs of the stabilizer or to one leg with firm clamping of the opposite leg. This kind of testing device has the disadvantage that the testing frequency can hardly exceed 5 Hz, since the forces of mass that cannot be compensated lead to extreme vibration of the testing stand, of the floor, etc. The low frequency of the cycling of the load leads to an extremely long duration of the test on the individual part (about 50 hours for 1,000,000 cycles of the load at 5 Hz cycling of the load frequency). The long test time makes the development of stabilizers difficult, and unacceptably delays results of random testing of production parts. Another problem of the eccentric drive is that only oscillation tests with constant amplitudes can be carried out in such test stands.

Servo-hydraulic test systems are known for obtaining stress profiles closer to in use profiles in which a plurality of different amplitudes are applied to the part. These testing systems are not only extremely expensive to manufacture but also cause vibrations on the adjustment location due to forces of gravity that cannot be compensated and are very costly to operate.

OBJECTS AND SUMMARY OF THE INVENTION

Departing from the above mentioned prior art, the object of the invention is a process and an apparatus for testing stabilizers in a simple, economic manner and considerably quicker than formerly accomplished.

According to the process of the invention, this problem is solved by exciting the legs of a stabilizer to be tested together with movable mass elements attached thereto at the resonant frequency of the mass-spring system with out of phase oscillations about a firm zero point. The apparatus of the invention comprises a drive means having movable mass elements which, with the stabilizer, forms a mass-spring resonator. The movably disposed mass elements are each connected with one leg of the stabilizer in a manner such that, via an attached oscillation exciter together with the stabilizer legs, they can be brought to oscillations whose frequency is determined by the mass of the mass elements and the spring tension of the stabilizer.

The principle of the invention is that by attaching the mass to each leg, an intrinsically closed system is formed. The system is capable of oscillating the stabilizer as the test piece and the other parts are two parts located in the testing apparatus. In the process of the invention, the oscillation exciter must only balance the losses occurring in the system, that is, friction resulting from the movement of the apparatus, air damping and material damping. Thus, the resulting requirement of energy is extremely small (below 1 kw for testing the stabilizer of a mid-size passenger car).

Especially suited as an oscillation exciter, because of its adjustability, is a disk armature motor. The disk armature motor causes a mass element to reciprocally rotate. The reciprocally rotatable mass element is rotatably supported about an axle via a shaft and is fastened at one end to the stabilizer leg. The other stabilizer leg is coupled with a second rotatable mass element shaped in a manner such that it can oscillate out of phase with the first mass element. The total load amplitude applied to the stabilizer doubles with a constant oscillation amplitude (angle of rotation) of the oscillation exciter or of the first mass element. The moments of inertia on both sides (seen from the center of the test piece) must be equal.

In a preferred embodiment of the invention, the mass elements are provided with compensating mass elements arranged on the side of the mass elements opposite the bearing axle and constructed, with regard to dimensions, in a manner such that the mass elements are statically counterbalanced about their axes of rotation. Therefore, in the preferred embodiments of the invention, the mass elements together with the compensating mass elements have inertia moments that act purely rotationally and reciprocally compensate each other in a manner such that no oscillations are transmitted outwardly (to the assembly floor).

In the above apparatus, where the mass elements are each supported, there can obviously be also tested torsion springs (torsion bar) instead of a stabilizer in which case the coupling means between the mass elements and the ends of the torsion spring must be constructed accordingly.

In another preferred embodiment of the invention, as shown in FIGS. 7 and 8, the mass elements are not supported, but are each rotatably mounted via clamping elements directly on clamping ends of the stabilizer legs, thereby insuring the introduction of a torque-free force like in the vehicle. The oscillation exciter is connected via coupling means with one stabilizer leg. The coupling means preferably comprise a coupling lever lockable at one end on the stabilizer leg and by its other end pivotally retained in a bearing means about an axle. The coupling lever axle extends perpendicular to the center line through the stationary bearing means. The bearing axle means pivotally connected to the coupling lever is connected to a reciprocally movable rotating oscillation exciter whose axis of rotation is aligned with the center line. In this arrangement, the adaptation of the apparatus to different shapes of stabilizers is made possible in an especially easy manner and the construction of the arrangement is simplified by the elimination of the two bearings for the mass elements.

BRIEF DESCRIPTION OF THE DRAWINGS

Other essential features of the invention result from the description that follows of a preferred embodiment of the invention which is explained in detail with reference to the drawings.

DETAILED DESCRIPTION OF THE PREFERRED EMBODIMENTS

In the description that follows, the same numerals have been used for the same or equivalent parts.

Figure 1:
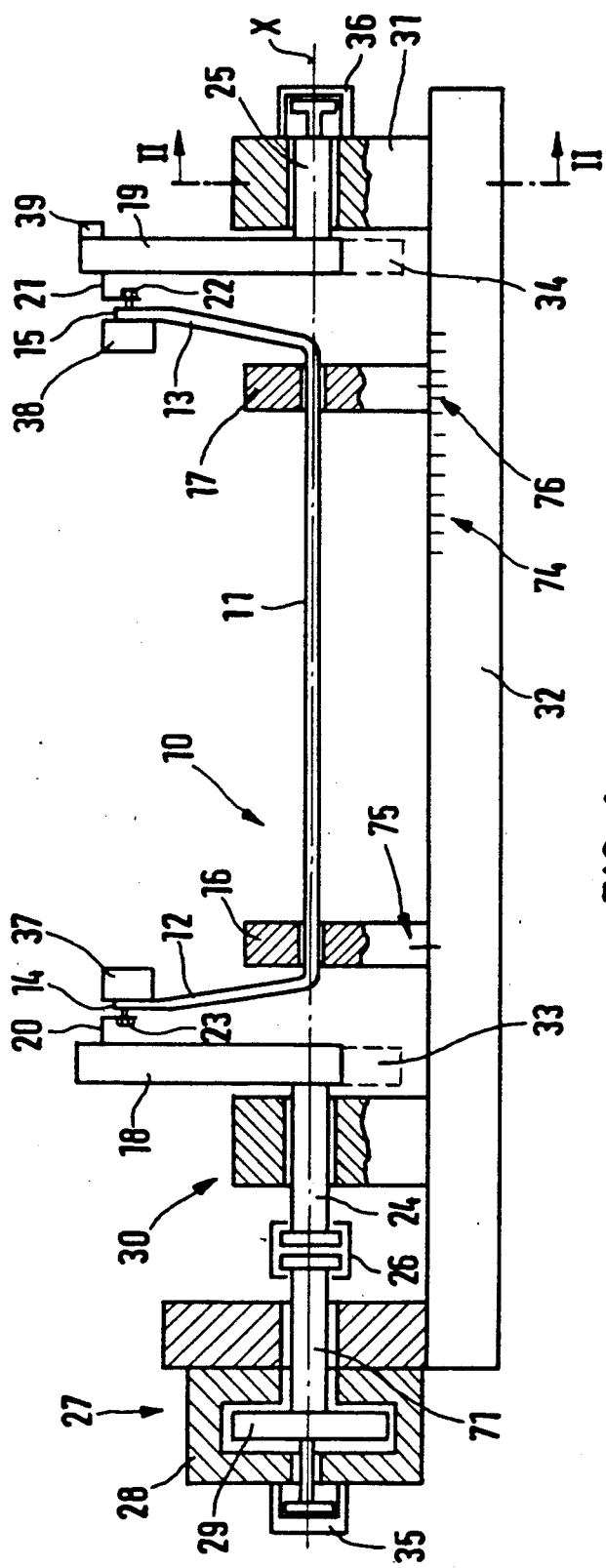
FIG. 1 is a diagrammatic, partially in section, side view of an apparatus according to one embodiment of the invention.

As shown in FIG. 1, the embodiment of the apparatus comprises a bench 32 upon which are fixed two bearings 16, 17 in which a stabilizer 10 to be tested is rotatably mounted at two points of its central section 11. The stabilizer 10 to be tested is also supported by such points on the chassis of the vehicle on which it is mounted.

In addition, there is fixed on the bench 32, bearings 30 and 31 of the mass elements in each of which is rotatably, movably supported a substantially rod-shaped mass elements 18 or 19 by means of its shaft 24 or 25. The shafts 24, 25 of the mass elements 18, 19 have a common axis of rotation X which represents at the same time the center line that extends through the stabilizer bearings 16 and 17.

The shaft 24 of the mass element 18 is non-rotatably connected via a shaft coupling 26 with the motor shaft 71 of a disk armature motor 27 whose disk-shaped rotor 29 is fixed on the motor shaft 71 and whose stator 28 is fastened on the bench 32.

The mass elements 18 and 19 are connected via coupling elements 20, 21 and clamping bolts 22, 23 with the clamping ends 14, 15 of the stabilizer 10. Coupling elements 20, 21 which are described in further detail hereinbelow, are constructed in a manner such that they can only transmit forces that act upon the plane normal to the axis of rotation X, while forces parallel or perpendicular to the axis of rotation X lead only to a deformation of the coupling elements 20, 21.

On the clamping ends 14, 15 of the stabilizer 10 to be tested, there are mounted synchronizing elements 37, 38 which (in addition to the mass elements 18, 19) determine the resonant frequency of the system.

To the mass element 19 which is not coupled with the disk armature motor 27, is attached a compensation element 39 dimensioned in a manner such that the total mass moments of inertia of the mass are equal on both sides of the stabilizer 10. Since the mass moments of inertia of the shafts 24 and 25 are substantially equal and those of the coupling 26 and of the motor shaft 71 are almost negligible, the compensation element 39 thus substantially compensates the moment of inertia of the rotor 29 of the disk armature motor 27.

As further shown in FIG. 1, there are coupled with each shaft 24 or 25 of the mass elements, angle indicators 35 or 36, the output signals of which measure the respective angular position (relative to the axis of rotation X) of the mass elements 18 and 19, and thus of the legs 12 and 13 of the stabilizer 10 to be tested.

Figure 2:
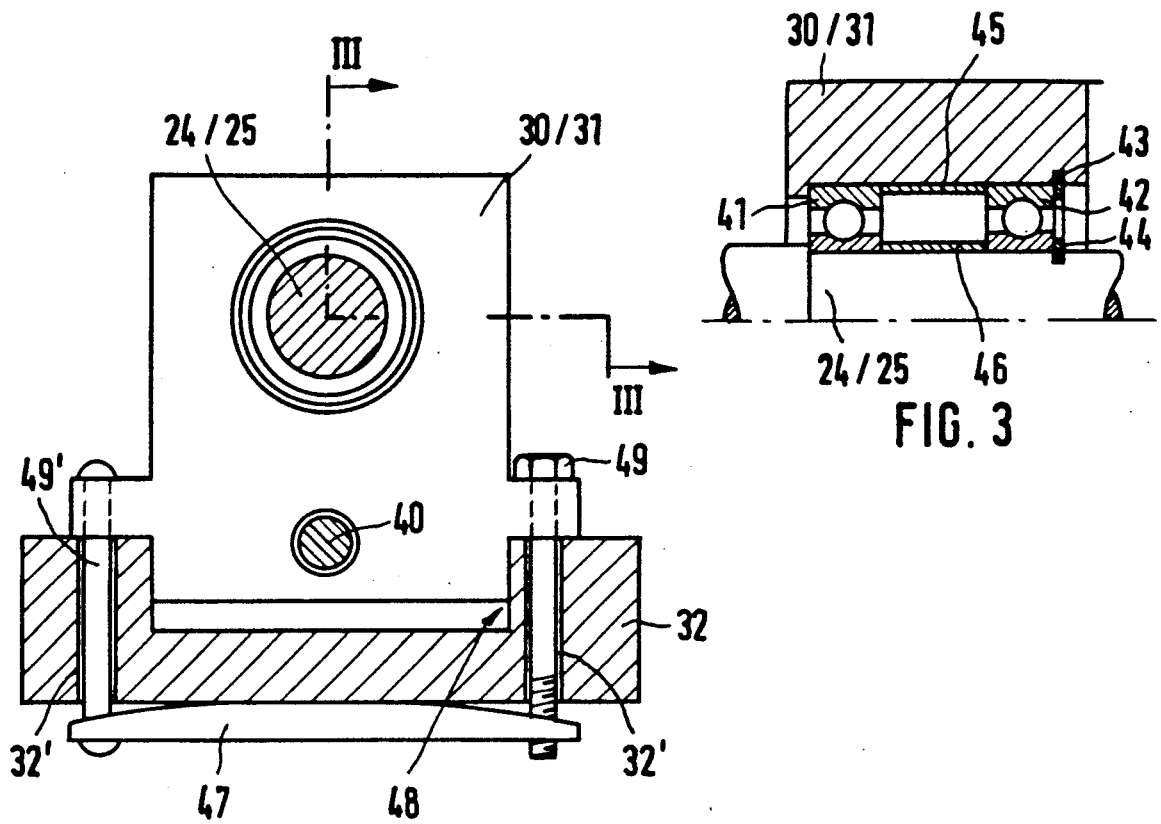
FIG. 2 is a longitudinal sectional view, taken along line II—II of FIG. 1.
Figure 3:
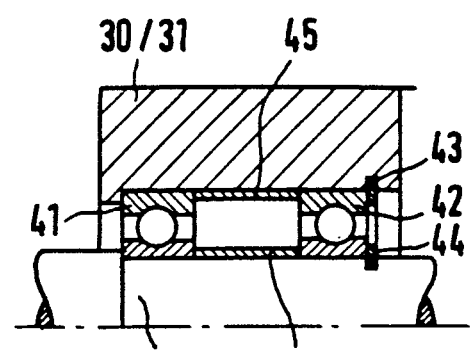
FIG. 3 is a partial longitudinal sectional view, taken along line III—III of FIG. 2.

Hereinbelow are described in detail, with reference to FIGS. 2 and 3, the bearings 30 and 31 of the mass element which are designed substantially similar or identical.

Each bearing 30 or 31 of the mass elements has a bore in which are lodged two roller bearings 41, 42 kept apart by spacer sleeves 45, 46 and held on the shaft 24 or 25 to be supported in the bearings 30 and 31 of the mass elements by guard rings 43, 44. The bearings 30, 31 of mass elements 18, 19 are each slidingly supported in a guide 48 in the bench 32, it being possible optionally to provide for the displacement along a spindle 40 with a motor drive. The bench 32 has on both sides of the guide 48, slots 32' shaped in a manner such that locking bolts 49, 49' clamped by one end on respective bearings 30 and 31 of the mass elements can project through the slots 32', the ends of the locking bolts 49, 49' situated below the bench 32 being connected with each other via a clamping beam 47. One bolt 49' is not adjustable, while the other bolt 49 is engaged by its lower end in a corresponding threaded hole in the clamping beam 47 so that when the bolt 49 is tightened, the clamping beam 47 is drawn to the bench 32 and the bearings 30 and 31 of the mass elements are fixed thereon.

This configuration of the guide is also especially well suited for the stabilizer bearings 16, 17, wherein one of the bearings (in FIG. 1 the bearing 17) is preferably provided with a measuring mark 76 for a scale 74 on the bench 32. The other bearing 16 is firmly mounted at a zero mark 75 on the bench 32, the scale 74 indicating the distance between the marks 75 and 76 or between the bearings 16 and 17.

The bearing 17 is manually or electromotively adjustable via a spindle so that the arrangement can be adjusted to the size of the test piece very easily and precisely.

Figure 4:
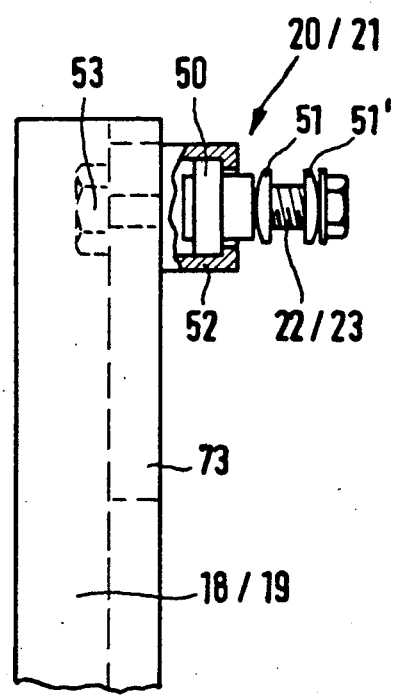
FIG. 4 is a side view, partially in section, of an end section of a mass element with a coupling element.

The coupling element 20 or 21 indicated in FIG. 1 as an L-shaped metal plate is preferably designed in the manner shown in FIG. 4. The mass elements 18 or 19 are here provided with a slot 73 extending over part of their length (normal to the axis X), so that a sliding carriage 52 can be fastened via a clamping bolt 53 on each mass element 18 or 19 at a variable distance from the axis of rotation. In the sliding carriage 52 a roller bearing 50 is held with its outer ring and in whose inner ring a clamping bolt 22 or 23 is threadable in order to connect the clamping end 14 or 15 of a stabilizer leg 12 or 13, which end is provided with a corresponding bore, with the component mass element 18 or 19. To avoid stressing the stabilizer leg when tightening the bolt 22 or 23, spherical disks 51, 51' are inserted on both sides of the clamping end 14 or 15 of the stabilizer. Owing to this design of the coupling elements 20, 21, it is possible to prevent essential deformations of the stabilizer leg which could affect the result of the test.

Hereinbelow are described, in more detail, the bearings 16, 17 by which the stabilizer 10 to be tested is supported on the bench 32.

Figure 5:
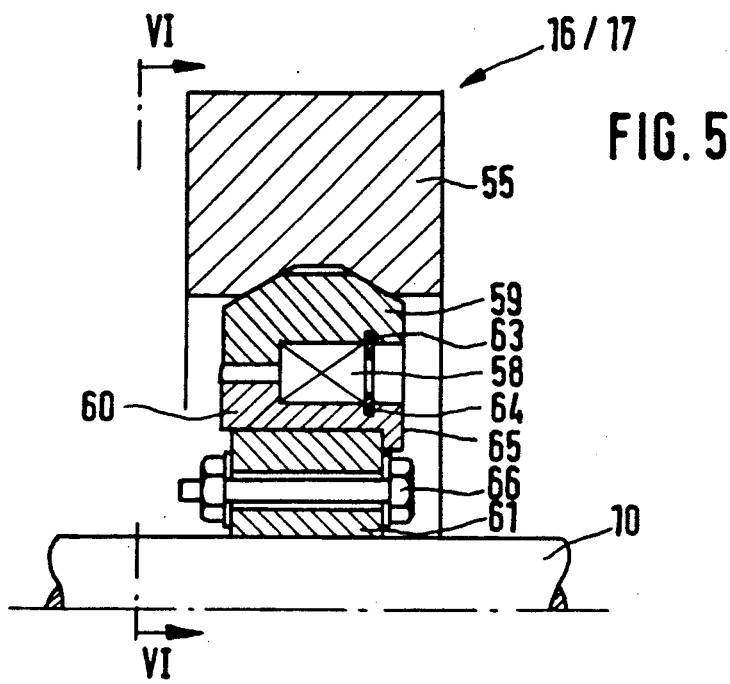
FIG. 5 is a partial longitudinal sectional view through the top part of a bearing element, taken along line V—V of FIG. 6.
Figure 6:
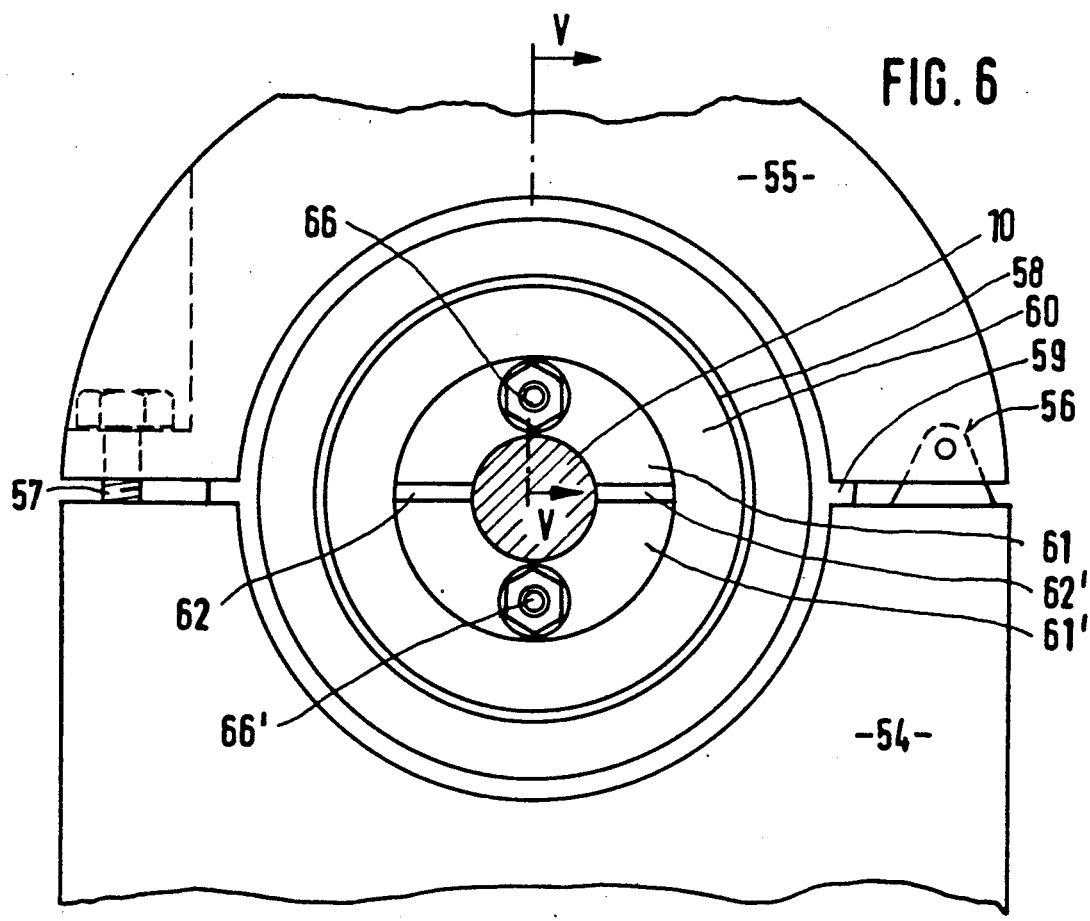
FIG. 6 is a front view, taken along line VI—VI of FIG. 5.

As shown in FIGS. 5 and 6, the bearings each comprise self-aligning roller bearings 58 which rotatably connect an outer ring 59 with an inner ring 60. In the inner and outer ring, the bearing 58 is locked by clamping rings 63, 64 so that the outer ring 59 is firmly but rotatably connected with the inner ring 60 in an axial direction.

Between the inner ring 60 and the stabilizer 10, there are inserted two halves of holding disks 61, 61' each having one bore (preferably at the center) in which are arranged clamping bolts 66, 66'. The outer and inner diameters of the holding disks 61, 61' are dimensioned in a manner such that when the clamping bolts 66, 66' are not tightened, the holding disks 61, 61' are insertable in the space between stabilizer 10 and inner ring 60 until abutting against a radially inwardly projecting collar 65 on the inner ring 60. The holding disks 61, 61' are made of a flexible synthetic material so that when the clamping bolts 66, 66' are clamped, the material of the holding disks 61, 61' radially expands outwardly and inwardly and thus the holding disks 61, 61' expand between the inner ring 60 and the stabilizer 10. The selection of material provides not only this hold which is extremely simple to mount and dismount but also prevents any frictional wear on the test piece which would be inevitable with a metal bearing.

The outer ring 59 of the arrangement preferably has a cross section that tapers frusto-conically so that the outer ring 59 can be clamped in a properly designed groove with a hollow wedge-shaped cross section in a socket 54 with a cap 55 of a bearing block. The cap 55 is connected with the socket 54 by a hinge 56 on one side and by a clamping bolt 57 on the other side. This arrangement for removing the bearing elements 58–60 is necessary at least for one bearing (16 or 17) while the bearing elements 58 to 60 can each be firmly mounted in the other bearing 16 or 17 so that a stabilizer 10 to be tested is first mounted on one bearing and then the bearing elements 58 to 60 are threaded on the other end until reaching the correct position in the open second bearing block. Finally, the cap 55 of this bearing is connected with the socket 54 via the clamping bolt 57. The holding disks 61, 61' are then inserted and the bolts 66, 66' tightened.

Another preferred embodiment of the invention is explained, in detail, hereinbelow with reference to FIGS. 7 and 8.

The essential difference from the arrangement shown above is that here the mass elements 18 and 19 are not supported but are directly mounted on the clamping ends 14 and 15. In FIG. 7, only one side of the stabilizer is shown, the other side or the other leg, being connected with similar mass elements.

Figure 7:
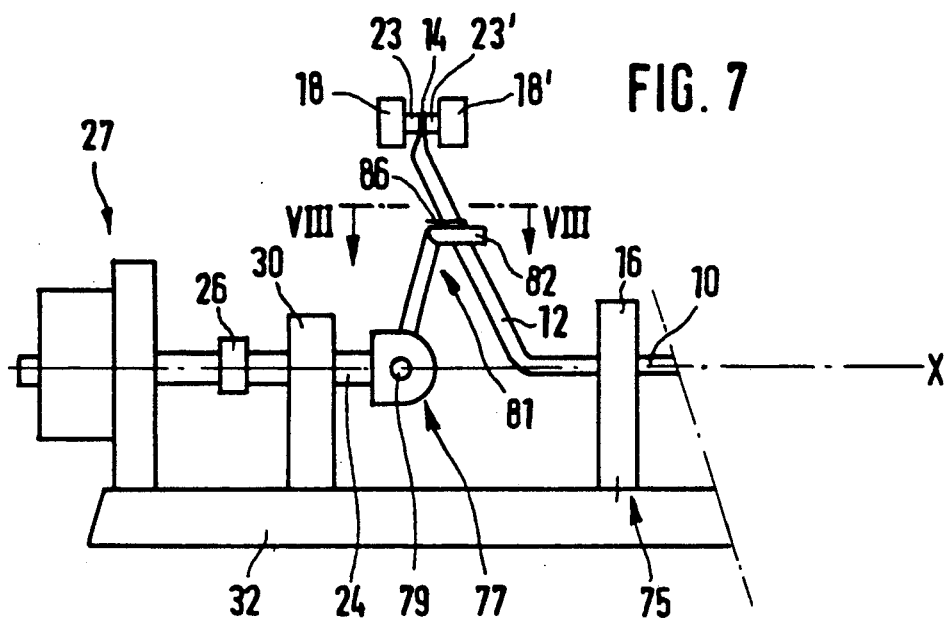
FIG. 7 is a partial side view of another preferred embodiment of the invention.
Figure 8:
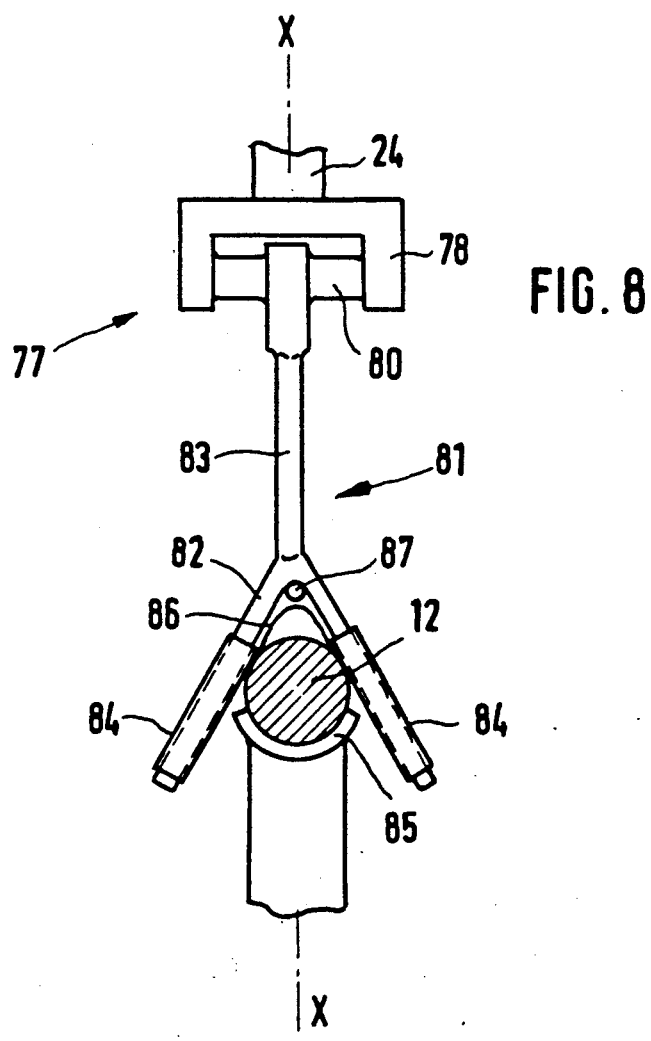
FIG. 8 is a cross-sectional view, taken along line VIII—VIII of FIG. 7.

In order to allow forces as uniform as possible to act on the stabilized legs 12 and 13, it is preferred that the mass elements are divided in two, as shown in FIG. 7, wherein bearings 23, 23' are provided between the parts of mass elements 18, 18' and the respective clamping end 14 (or 15) of the stabilizer leg 12 (or 13).

The oscillatory excitation takes place in this preferred embodiment via a coupling lever 81 which, by one end, is lodged in a bearing 77. The bearing 77 has a relatively wide bearing yoke 78 in which is fastened a bearing axle 80 and a bracket 83 projecting therefrom. The yoke 78 is fastened on the shaft 24 in a manner such that the axis of rotation X of the shaft 24 extends through the axis of rotation of the bearing 77 at a right angle. The bracket 83 thus has a rotation point 79 that coincides with the intersection point of the axis X and the axis of rotation of the bearing 77.

At its end opposite the bearing 77, the bracket 83 has a V-shaped yoke 82 whose legs are each coated with a protective tube 84 of synthetic material. The yoke 82 is preferably offset in respect to the bracket 83. In this arrangement, it is possible, when clamping a test piece 10, to first fold back (to the left in FIG. 7) the coupling lever 81. After clamping the stabilizer test piece, the coupling lever 81 is folded forward (clockwise in FIG. 7) in a manner such that the stabilizer leg 12 comes to lie in the yoke 82. Accordingly, the coupling lever 81 is connected with the leg 12 via a gripping yoke 85 and a tension belt 86 which can be hung on a lug 87 on the coupling lever 81. The coupling lever 81 is preferably made of light metal so that the arrangement has only a slight mass moment of inertia. In this design of the invention, there can be achieved an increase of the resonant frequency of the system and an easier change of test pieces. If needed, there can be provided on the other side of the stabilizer 10, not shown in FIG. 7, a "blind coupling lever" that is likewise supported and has a moment of inertia corresponding to that on the driving side. On this "blind coupling lever", on the other side, as in the embodiment of FIG. 1, there can be provided a second indicator of the angle of rotation. The bearings 16 and 17 are adjustable, as has been described with regard to FIG. 1.

Figure 9:
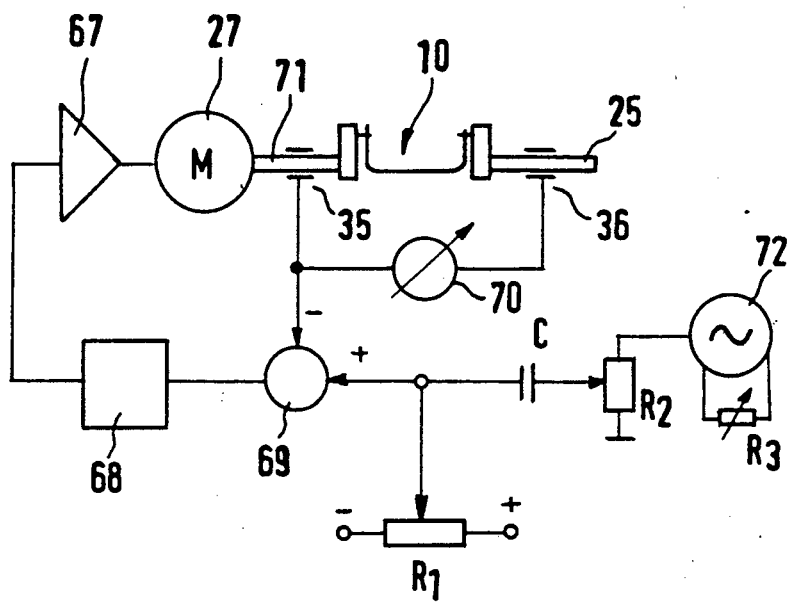
FIG. 9 is a diagrammatic block diagram of the electric circuit of the whole system.

The basic principle of the drive of the apparatus described is explained in further detail with reference to FIG. 9, wherein the individual elements of the arrangement are known already.

The motor 27 is supplied with a current via a servo-amplifier 67 having its control input connected with the output of a regulator 68. The regulator 68 is connected by its input with the output of a compensator 69 at the positive input of which appears a set point value which is compared with the output signal of the angle indicator 35 via the inverting compensator input thereof. According to the value at the set point input (+), the output shaft 71 of the motor 27 rotates by a certain angular amount.

The set point input of the comparator 69 is connected via a capacitor C and an amplitude-regulating potentiometer R2 with the output of a sinusoidal generator 72 whose output frequency is adjustable by a correcting element R3. In addition, a direct current potential is passed to the set point input (+) of the comparator 69 via an adjusting means R1.

Between the outputs of both angle indicators 35 and 36 is inserted a measuring means 70, the arrangement being such that the phase relationship between the output signals of both angle indicators 35 and 36 can be measured or shown.

When testing a stabilizer 10 (after the mechanical preparations described above), what is done first is to adjust via the adjusting means R1, the idle position in which the legs 12 and 13 of the stabilizer 10 project substantially vertically upwards. Then the output frequency of the sinusoidal generator 72 (at low amplitude) is adjusted via the adjusting means R3 to the resonant frequency of the system. The resonant frequency is reached when the output signal of the angle indicator 35 is 180° out of phase with the output signal of the angle indicator 36. The desired amplitude can then be adjusted, it being possible to effect the adjustment not only manually (via the adjusting means R2) but also "program controlled" via a standard program according to which different load amplitudes are successively passed through.

In another embodiment, there are no rotation angle indicators provided for adjusting the resonant frequency. A feedback control loop, which forms together with the attached mass-spring mass system, a closed oscillation circuit is provided. The current fed to the motor 27 can be used as a control quantity since it becomes minimal when the resonant frequency is reached.

A single rotation angle indicator on the motor 27 is then sufficient to adjust the zero point position.

We claim:

1. A process for testing a vehicle stabilizer using a vehicle stabilizer apparatus, wherein said stabilizer has a central section and two legs, said vehicle stabilizer apparatus being comprised of, in combination:

stationary bearing means for clamping a stabilizer;

motor driving means for rotating the stabilizer and moving one leg of the stabilizer relative to the other leg of the stabilizer, said motor driving means including two movable mass elements which form a mass-spring resonator with the stabilizer, each connected with a leg of the stabilizer; and an attached oscillation exciter means for oscillating said stabilizer legs in out of phase oscillations whose frequency is determined by the mass elements and spring tension of the stabilizer, said process comprising clamping the central section of said stabilizer and oscillatingly exciting said legs, together with said movable mass elements attached thereto, with out of phase oscillations with rotation around a firm zero point by said oscillation exciter means at a resonant frequency determined by the mass elements and spring tension of the stabilizer.

2. An apparatus according to claim 1, further including shaft means for rotatably moving said mass elements around an axis aligned with a center line through the stationary bearing means.

3. An apparatus according to claim 2, further including coupling means for connecting said mass elements with clamping ends of said stabilizer legs, said coupling means being constructed in a manner such that forces that substantially act exclusively in a plane perpendicular to said center line are transmittable between said mass elements and said stabilizer legs.

4. An apparatus for testing vehicle stabilizers wherein said stabilizers have a central section and two legs, said apparatus comprised of, in combination:

stationary bearing means for clamping a stabilizer;

motor driving means for rotating the stabilizer and moving one leg of the stabilizer relative to the other leg of the stabilizer, said motor driving means including two movable mass elements which form a mass-spring resonator with the stabilizer, each connected with a leg of the stabilizer;

shaft means for rotatably moving said mass elements around an axis aligned with a center line through the stationary bearing means, each of said mass elements provided with compensating elements arranged on a side of each of said mass elements opposite to said center line and having dimensions such that the mass elements are staticly counterbalanced about their axis of rotation; and an attached oscillation exciter means for oscillating said stabilizer legs in out of phase oscillations whose frequency is determined by the mass elements and spring tension of the stabilizer.

5. An apparatus for testing vehicle stabilizers wherein said stabilizers have a central section and two legs, said apparatus comprised of, in combination:

stationary bearing means for clamping a stabilizer;

motor driving means for rotating the stabilizer and moving one leg of the stabilizer relative to the other leg of the stabilizer, said motor driving means including two movable mass elements which form a mass-spring resonator with the stabilizer, each connected with a leg of the stabilizer;

shaft means for rotatably moving said mass elements around an axis aligned with a center line through the stationary bearing means; roller bearings having a rotation axis which extends substantially parallel with said center line for connecting said mass elements with clamping ends of said stabilizer legs, said roller bearings being constructed in a manner such that forces that substantially act exclusively in a plane perpendicular to said centerline are transmittable between said mass elements and said stabilizer legs; and an attached oscillation exciter means for oscillating said stabilizer legs in out of phase oscillations whose frequency is determined by the mass elements and spring tension of the stabilizer.

6. An apparatus for testing vehicle stabilizers wherein said stabilizers have a central section and two legs, said apparatus comprised of, in combination:

stationary bearing means for clamping a stabilizer;

motor driving means for rotating the stabilizer and moving one leg of the stabilizer relative to the other leg of the stabilizer, said motor driving means including two movable mass elements which form a mass-spring resonator with the stabilizer, each connected with a leg of said stabilizer;

an attached oscillation exciter means for oscillating said stabilizer legs in out of phase oscillations whose frequency is determined by the mass elements and spring tension of the stabilizer;

clamping bearing means for rotatably clamping said mass elements directly on clamping ends of said stabilizer legs;

rotation means; and coupling means for connecting said rotation means and said oscillation exciter means with one stabilizer leg.

7. An apparatus according to claim 6, wherein said coupling means comprise one coupling lever lockable by one end thereof on said stabilizer leg and pivotally held by another end thereof on a bearing about one axle which extends perpendicular to a center line through the stationary bearing means, said bearing being connected with a rotating, reciprocally oscillating exciter whose rotation axis is aligned with said center line.

8. An apparatus for testing vehicle stabilizers wherein said stabilizers have a central section and two legs, said apparatus comprised of, in combination:

stationary bearing means for clamping a stabilizer;

motor driving means for rotating the stabilizer and moving one leg of the stabilizer relative to the other leg of the stabilizer, said motor driving means including two movable mass elements which form a mass-spring resonator with the stabilizer, each connected with a leg of said stabilizer; and a disk armature motor for oscillating said stabilizer legs in out of phase oscillations whose frequency is determined by the mass elements and spring tension of the stabilizer.

9. An apparatus according to claim 1, further including a measuring element means connected with said oscillation excite means and connected with a measuring element for detecting oscillating movement of said legs.

10. An apparatus according to claim 9, further including motor regulator means for adjusting the motor driving means to a set point in response to said measuring element.

11. An apparatus according to claim 10, wherein said measuring element means comprises an indicator of an angle of rotation and the motor regulator means is constructed in a manner such that rotary movement of he motor driving means results in a firmly adjustable angular value with a symmetrical amplitude.

* * * * *